United States Patent [19]

Shutske

[11] Patent Number: 4,942,237
[45] Date of Patent: Jul. 17, 1990

[54] METHOD OF PREPARING ISOXAZOLO(5,4,3-KL)ACRIDINES

[75] Inventor: Gregory M. Shutske, Somerset, N.J.

[73] Assignee: Hoechst-Roussel Pharmaceuticals Inc., Somerville, N.J.

[21] Appl. No.: 494,188

[22] Filed: Feb. 12, 1990

Related U.S. Application Data

[62] Division of Ser. No. 364,420, Jun. 9, 1989, Pat. No. 4,920,117.

[51] Int. Cl.$^5$ ............................................. C07D 498/06
[52] U.S. Cl. ....................................................... 546/64
[58] Field of Search ........................................... 546/64

[56] References Cited

PUBLICATIONS

Oppolzer et al., *Tetrahedron Letters*, (1970), No. 13, pp. 1117–1120.

*Primary Examiner*—Robert W. Ramsuer
*Attorney, Agent, or Firm*—Tatsuya Ikeda

[57] ABSTRACT

There are disclosed compounds having the formula

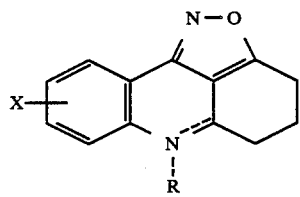

where
  X is hydrogen, loweralkyl, loweralkoxy, halogen or trifluoromethyl, and
  R when present is hydrogen, loweralkyl, allyl, aryl-loweralkyl,

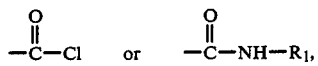

wherein $R_1$ is loweralkyl, —CH$_2$C≡CH,

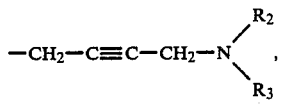

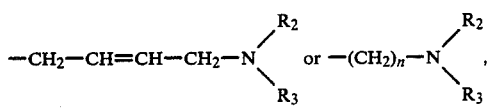

n being 2, 3 or 4 and $R_2$ and $R_3$ being independently loweralkyl, or the group

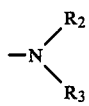

taken as a whole constituting

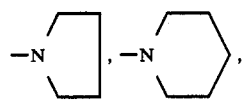

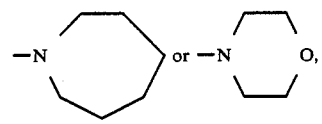

which compounds are useful as analgesic agents and also for the treatment of various memory dysfunctions characterized by a decreased cholinergic function such as Alzheimer's disease.

2 Claims, No Drawings

METHOD OF PREPARING ISOXAZOLO(5,4,3-KL)ACRIDINES

This is a division of application Ser. No. 364,420, filed Jun. 9, 1989, now U.S. Pat. No. 4,920,117.

This invention relates to compounds having the formula

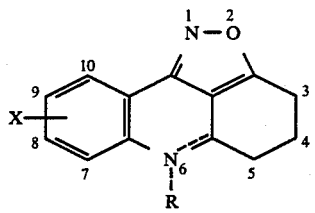

where
X is hydrogen, loweralkyl, loweralkoxy, halogen or trifluoromethyl, and
R when present is hydrogen, loweralkyl, allyl, aryl-loweralkyl,

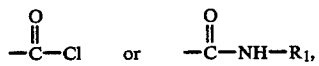

wherein $R_1$ is loweralkyl, $-CH_2C\equiv CH$,

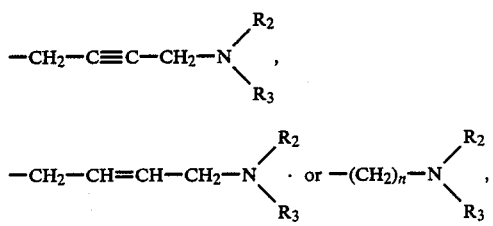

n being 2, 3 or 4 and $R_2$ and $R_3$ being independently loweralkyl, or the group

taken as a whole constituting

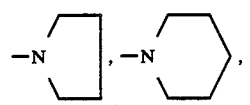

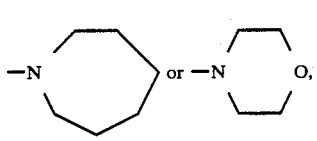

which compounds are useful as analgesic agents and also for the treatment of various memory dysfunctions characterized by a decreased cholinergic function such as Alzheimer's disease.

The dotted lines appearing in Formula I and other formulas used in this specification and appended claims signify the fact that when the group R is present, the chemical bond between the 5a-carbon and 6-nitrogen is a single bond and that when R is absent, the bond between the 5a-carbon and 6-nitrogen is a double bond.

Throughout the specification and the appended claims, a given chemical formula or name shall encompass all stereo, geometrical and optical isomers thereof where such isomers exist, as well as pharmaceutically acceptable acid addition salts thereof and solvates thereof such as for instance hydrates.

The following definitions shall apply through the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term halogen shall mean fluorine, chlorine, bromine or iodine.

Unless otherwise stated or indicated, the term aryl shall mean a phenyl group optionally mono-substituted with a loweralkyl, loweralkoxy, halogen or trifluoromethyl group.

The compounds of this invention can be prepared by utilizing one or more of the synthetic steps described below.

Throughout the description of the synthetic steps, the definitions of X, R, $R_1$, $R_2$, $R_3$ and n are as given above unless otherwise stated or indicated, and other nomenclatures shall have their respective meanings given in their first appearances.

STEP A:

A compound of Formula II is allowed to react with hydrazoic acid ($HN_3$) in the presence of a protic acid or Lewis acid to afford a compound of Formula III. This reaction is typically conducted by using $NaN_3$ and concentrated $H_2SO_4$ as well as a suitable medium such as dichloromethane at a temperature of about 0° to 40° C.

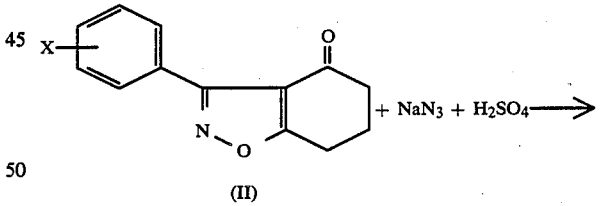

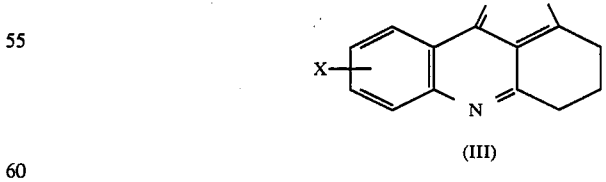

The starting compound of Formula II where X is hydrogen is disclosed in Akhrem et al., *Synthesis*, page 43 (1978).

STEP B:

Compound III is allowed to react with $NaCNBH_4$ in a routine manner known to the art to afford a compound of Formula IV.

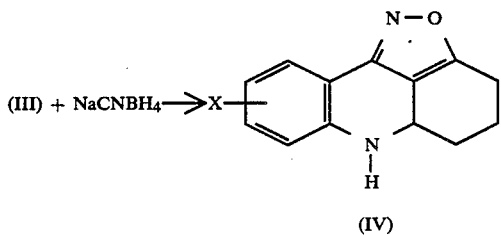

(III) + NaCNBH₄ → (IV)

STEP C:
Compound IV is allowed to react with a halide compound of the formula R₄-Hal, where R₄ is loweralkyl, allyl or arylloweralkyl and Hal is chlorine or bromine, to afford a compound of Formula V.

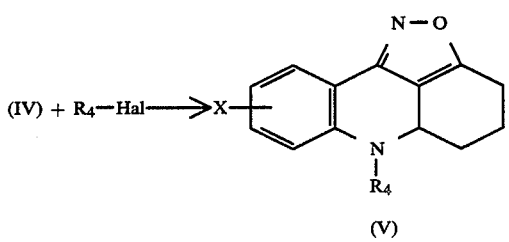

(IV) + R₄—Hal → (V)

The above reaction is typically conducted in the presence of an inorganic base such as $K_2CO_3$ and a suitable medium such as dimethylformamide at a temperature of about 25° to 100° C.

STEP D:
Compound IV is allowed to react with phosgene to afford a compound of Formula VI.

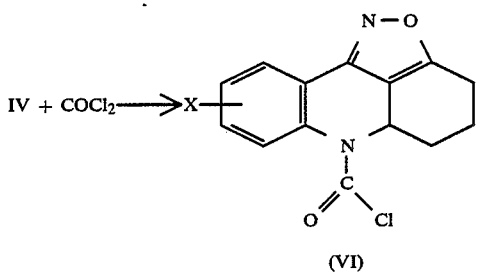

IV + COCl₂ → (VI)

The above reaction is typically conducted in the presence of a suitable acid scavenger such as triethylamine and a suitable solvent such as dichloromethane at a temperature of about 0° to 40° C.

STEP E:
Compound VI is allowed to react with an amine of the formula

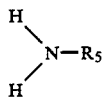

where R₅ is loweralkyl,

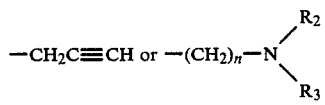

to afford a compound of Formula VII.

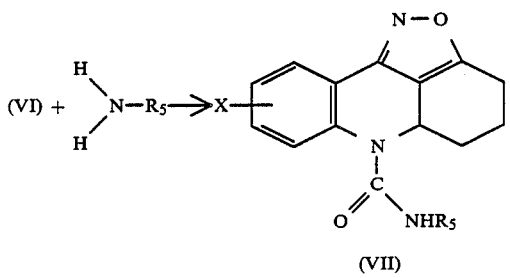

(VI) + H₂N—R₅ → (VII)

The above reaction is typically conducted in a suitable solvent such as carbon tetrachloride at a temperature of about 0° to 45° C.

STEP F:
As an alternative to STEPS D and E, compound IV is allowed to react with an isocyanate of the formula R₅-NCO to afford compound VII.

(IV)+R₅-NCO→(VII)

The above reaction is typically conducted in a suitable solvent such as carbon tetrachloride at a temperature of about 0° to 45° C.

STEP G:
A compound of Formula VIIa obtained in STEP E or F is allowed to react with formaldehyde and a secondary amine of the formula

to afford a compound of Formula VII (Mannich reaction).

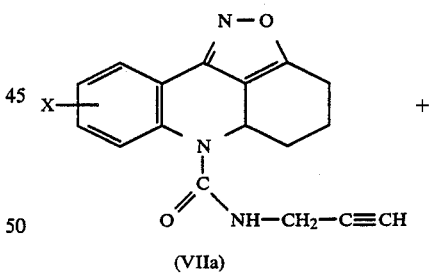

(VIIa)

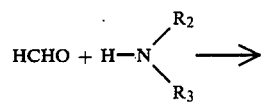

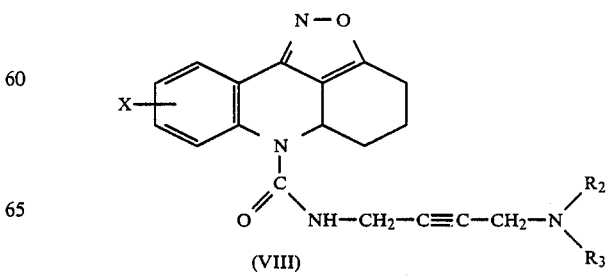

(VIII)

The above reaction is typically conducted in the presence of a catalytic amount of cuprous chloride (CuCl) and a suitable solvent such as tetrahydrofuran at a temperature of about 50° to 150° C.

STEP H:

Compound VIII is converted to a cis or trans double bond compound of Formula IX.

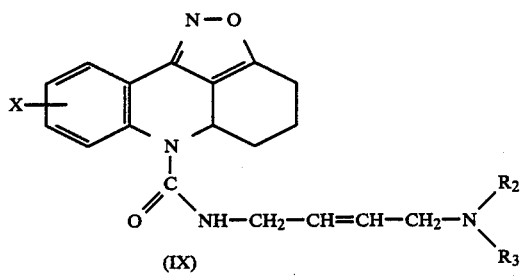

(VIII) ⟶

(IX)

For preparing the trans isomer, typically this reaction is conducted with the aid of lithium aluminum hydride and a suitable medium such as THF at a temperature of about 0° to 80° C. For preparing the cis isomer, typically this reaction is conducted with the aid of a suitable catalyst such as 5% Pd/BaSO₄ and a suitable medium such as methanol at a temperature of about 25°-50° C.

STEP I:

Compound VIII is catalytically hydrogenated in a routine manner known to the art to afford a compound of Formula X.

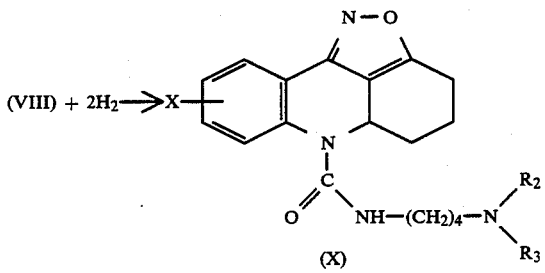

(VIII) + 2H₂ ⟶

(X)

Typically this reaction is conducted with the aid of a suitable catalyst such as 5% Pd/C and a suitable medium such as ethanol at a temperature of about 25° to 50° C.

The compounds of Formula I of the present invention are useful as analgesic agents due to their ability to alleviate pain in mammals. The activity of the compound is demonstrated in the 2-phenyl-1,4-benzoquinone-induced writhing test in mice, a standard assay for analgesia [Proc. Soc. Exptl. Biol. Med., 95, 729 (1957)]. Table 1 shows results of the test for of some of the compounds of this invention.

TABLE 1

| ANALGESIC ACTIVITY (Phenylquinone Writhing) | |
|---|---|
| Compound | Analgesic PQW, % Inhibition of Writhing at 20 mg/kg., s.c. |
| 6-Ethylaminocarbonyl-4,5,5a,6-tetrahydro-3H-isoxazolo-[5,4,3-kl]acridine | 44% |

TABLE 1-continued

| ANALGESIC ACTIVITY (Phenylquinone Writhing) | |
|---|---|
| N-[2-(4-Morpholinyl)ethyl]-4,5,5a,6-tetrahydro-3H-isoxazolo[5,4,3,-kl]acridine-6-carboxamide | 52% |
| N-(2-Propynyl)-4,5,5a,6-tetrahydro-3H-isoxazolo-[5,4,3-kl]acridine-6-carboxamide | 29% |
| N-[4-(1-Pyrrolidinyl)-2-butyn-1-yl]-4,5,5a,6-tetrahydro-3H-isoxazolo[5,4,3-kl]-acridine-6-carboxamide (Reference Compound) | 33% |
| Propoxyphene | 50% at 3.9 mg/kg, s.c. |

The compounds of Formula (I) of the present invention can also be used for the treatment of various memory dysfunctions characterized by a decreased cholinergic function such as Alzheimer's disease.

This utility can be ascertained by determining the ability of these compounds to inhibit the activity of the enzyme acetylcholinesterase and thereby increase the acetylcholine levels in the brain.

CHOLINESTERASE INHIBITION ASSAY

The ability to inhibit acetylchlinesterase was determined by the photometric method of Ellman et al., Biochem. Pharmacol. 7, 88 (1961). Results of some of the compounds of this invention are presented in Table 2 along with those of some reference compounds.

TABLE 2

| Cholinesterase Inhibition | |
|---|---|
| Compound | IC$_{50}$ (molar conc.) |
| 4,5-Dihydro-3H-isoxazolo-[5,4,3-kl]acridine | $3.9 \times 10^{-6}$ |
| 4,5,5a,6-Tetrahydro-3H-isoxazolo[5,4,3-kl]acridine (Reference Compounds) | $1.3 \times 10^{-5}$ |
| 9-Amino-1,2,3,4-tetrahydroacridine | $3.1 \times 10^{-7}$ |
| Physostigmine | $6.0 \times 10^{-9}$ |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incadescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of Dark Avoidance Assay for representative compounds of this invention and a reference compound are presented in Table 3.

TABLE 3

| | Dark Avoidance Assay | |
|---|---|---|
| Compound | Dose mg/kg body weight | % of animals with scopolamine induced memory deficit reversal |
| 4,5-Dihydro-3H-isoxazolo-[5,4,3-kl]acridine | 0.63 | 20% |
| 6-(2-Propenyl)-4,5,5a,6-tetrahydro-3H-isoxazolo-[5,4,3-kl]acridine | 1.25 | 27% |
| Physostigmine (Reference) | 0.31 | 20% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include
4,5-dihydro-3H-isoxazolo[5,4,3-kl]acridine;
4,5,5a,6-tetrahydro-3H-isoxazolo[5,4,3-kl]acridine;
6-(2-propenyl)-4,5,5a,6-tetrahydro-3H-isoxazolo[5,4,3-kl]acridine;
6-benzyl-4,5,5a,6-tetrahydro-3H-isoxazolo[5,4,3-kl]acridine;
6-(4-fluorobenzyl)-4,5,5a,6-tetrahydro-3H-isoxazolo[5,4,3-kl]acridine;
6-ethylaminocarbonyl-4,5,5a,6-tetrahydro-3H-isoxazolo[5,4,3-kl]acridine;
4,5,5a,6-tetrahydro-3H-isoxazolo[5,4,3-kl]acridine-6-carbonyl chloride;
N-[2-(4-morpholinyl)ethyl]-4,5,5a,6-tetrahydro-3H-isoxazolo[5,4,3-k]acridine-6-carboxamide;
N-(2-propynyl)-4,5,5a,6-tetrahydro-3H-isoxazolo[5,4,3-kl]acridine;
N-[4-(1-pyrrolidinyl)-2-butyn-1-yl]-4,5,5a,6-tetrahydro-3H-isoxazolo[5,4,3-kl]acridine-6-carboxamide;
N-[4-(4-morpholinyl)-2-butyn-1-yl]-4,5,5a,6-tetrahydro-3H-isoxazolo[5,4,3-kl]acridine-6-carboxamide;

The following examples are presented in order to illustrate this invention.

EXAMPLE 1

4,5-Dihydro-3H-isoxazolo[5,4,3-kl]acridine

3-Phenyl-4-oxo-4,5,6,7-tetrahydrobenz[1,2-d]isoxazole (6.0 g) was dissolved in 40 ml conc. $H_2SO_4$ and then dichloromethane (60 ml) was added. $NaN_3$ (2.0 g) was added portionwise at such a rate that foaming could be controlled. After 90 minutes, the reaction mixture was poured into ice/water and conc. HCl was added until the precipitated amine sulfate dissolved. The dichloromethane layer was separated and the aqueous phase was washed with additional dichloromethane. The aqueous phase was made basic with 50% NaOH and ice (up to pH 1–4) and then with $NaHCO_3$ (up to pH 8). The product was extracted into dichloromethane and then flushed over a short alumina column before concentration under reduced pressure. Recrystallization from EtOAc/hexane gave 1.85 g of product, m.p. 149°–150° C.

ANALYSIS: Calculated for $C_{13}H_{10}N_2O$: 74.27%C, 4.79%H, 13.33%N. Found: 74.50%C, 4.87%H, 13.39%N.

EXAMPLE 2

4,5,5a,6-Tetrahydro-3H-isoxazolo[5,4,3-kl]acridine

In 100 ml glacial acetic acid was dissolved 4.75 g 4,5-dihydro-3H-isoxazolo[5,4,3-kl]acridine. To the mechanically stirred solution under nitrogen was added 2.84 g of sodium cyanoborohydride. The reaction was complete after 0.5 hour at room temperature. The reaction mixture was neutralized with excess aqueous sodium carbonate and extracted with dichloromethane (DCM). The DCM was dried over MgSO$_4$, filtered and concentrated to a solid. The solid was purified by flash chromatography and recrystallized from 1:1 DCM/hexanes to yield 2.78 g of powder, m.p. 152°–154° C.

ANALYSIS: Calculated for C$_{13}$H$_{12}$N$_2$O: 73.57%C, 5.70%H, 13.20%N. Found: 73.84%C, 5.81%H, 13.22%N.

EXAMPLE 3

6-(2-Propenyl)-4,5,5a,6-tetrahydro-3H-isoxazolo[5,4,3-kl]acridine

In 20 ml dry dimethylformaldehyde (DMF) were combined 4.00 g 4,5,5a,6-tetrahydro-3H-isoxazolo[5,4,3-kl]acridine, 3.26 ml allyl bromide and 8 g milled K$_2$CO$_3$. The mixture was heated at 90° C. and mechanically stirred. Every hour 2 ml more allyl bromide was added. After 3 hours, the reaction was complete as observed by TLC. The mixture was partitioned between water and EtOAc. The EtOAc layer was concentrated to a solid which was purified by passing over a silica column (flash chromatography). The product obtained in this manner was recrystallized twice from 20% EtOAc/hexanes to yield 2.99 g solid which was dried in vacuo, m.p. 114°–117° C.

ANALYSIS: Calculated for C$_{16}$H$_{16}$N$_2$O: 76.16%C, 6.39%H, 11.10%N. Found: 75.90%C, 6.39%H, 11.15%N.

EXAMPLE 4

6-Benzyl-4,5,5a,6-tetrahydro-3H-isoxazolo[5,4,3-kl]acridine

In 50 ml dry DMF were combined 2.10 g 4,5,5a,6-tetrahydro-3H-isoxazolo[5,4,3-kl]acridine, 2.0 g milled anhydrous K$_2$CO$_3$ and 1.3 ml benzylbromide. The mechanically stirred mixture was heated under nitrogen at 90° C. for 18 hours. During the first 4 hours, 1 ml benzyl bromide was added every hour as TLC analysis indicated it was being consumed. For the work-up, the mixture was poured into excess water and extracted with DCM. The DCM layer was concentrated to an oil and the oil was purified on a silica column (flash chromatography) using DCM as an eluent. The product-containing fractions were combined and concentrated to a solid. The solid was recrystallized from EtOAc/hexanes and dried in a vacuum desiccator to yield 2.10 g of product, m.p. 162°–163.5° C.

ANALYSIS: Calculated for C$_{20}$H$_{28}$N$_2$O: 79.44%C, 6.00%H, 9.26%N. Found: 79.60%C, 6.23%H, 9.17%N.

EXAMPLE 5

6-(4-Fluorobenzyl)-4,5,5a,6-tetrahydro-3H-isoxazolo[5,4,3-kl]acridine

In 40 ml dry DMF were combined 3.00 g 4,5,5a,6-tetrahydro-3H-isoxazolo[5,4,3-kl]acridine, 8.8 ml 4-fluorobenzylbromide and 3 g milled K$_2$CO$_3$. The mixture was stirred mechanically under nitrogen at ambient temperature for 2 days during which the reaction was complete. The reaction mixture was poured into excess water and extracted with DCM. The DCM layer was concentrated to a residue and the residue was triturated with 1:1 methanol/water and recrystallized from 1:1 DCM/hexanes to yield after drying 2.21 g needles, m.p. 214° C. (dec.).

ANALYSIS: Calculated for C$_{20}$H$_{27}$FN$_2$O: 74.98%C, 5.35%H, 8.74%N. Found: 75.06%C, 5.52%H, 8.78%N.

EXAMPLE 6

6-Ethylaminocarbonyl-4,5,5a,6-tetrahydro-3H-isoxazolo[5,4,3-kl]acridine

In 20 ml CCl$_4$ were combined 5.00 g 4,5,5a,6-tetrahydro-3H-isoxazolo[5,4,3-kl]acridine and 9 ml ethyl isocyanate. The mixture was refluxed for two days. After the first day, 9 ml more ethyl isocyanate was added. The reaction mixture was then cooled in ice and the precipitate filtered. The precipitate was recrystallized from 1:1 DCM/hexanes and dried in vacuo at 80° C. to yield 3.91 g crystals, m.p. 189° C.

ANALYSIS: Calculated for C$_{10}$H$_{17}$N$_3$O$_2$: 67.83%C, 6.05%H, 14.83%N. Found: 67.82%C, 6.05%H, 14.84%N.

EXAMPLE 7

4,5,5a,6-Tetrahydro-3H-isoxazolo[5,4,3-kl]acridine-6-carbonyl chloride

In 50 ml of dichloromethane was dissolved 4.08 g of 4,5,5a,6-tetrahydro-3H-isoxazolo[5,4,3-kl]acridine. Phosgene in benzene (26 ml of 12.5% phogene in benzene) was then added all in one portion. This solution was then chilled with an ice/water bath as a solution of triethylamine (2.92 g) in 20 ml of dichloromethane was added dropwise. After the addition was complete (30 minutes), the reaction mixture was washed with dilute hydrochloric acid and then dried and concentrated. The residue obtained in this manner was recrystallized from dichloromethane/hexane to give 3.66 g of product, m.p. 189° C. (d).

ANALYSIS: Calculated for C$_{14}$H$_{11}$ClN$_2$O$_2$: 61.20%C, 4.03%H, 10.20%N. Found: 60.83%C, 4.13%H, 9.98%N.

EXAMPLE 8

N-[2-(4-Morpholinyl)ethyl]-4,5,5a,6-tetrahydro-3H-isoxazolo[5,4,3-kl]acridine-6-carboxamide In 100 ml CCl$_4$ were combined 2.50 g 4,5,5a,6-tetrahydro-3H-isoxazolo[5,4,3-kl]acridine-6-carbamoyl chloride and 1.43 ml 4-(2-aminoethyl)morpholine. The reaction mixture was refluxed ½ hour and 1.43 ml more of morpholine was added and reflux resumed for ½ hour more. The reaction mixture was diluted with DCM and washed with saturated NaHCO$_3$ solution. The organics were dried over MgSO$_4$, filtered and concentrated to a solid which was recrystallized once from 1:1 DCM/hexanes and once from 1:1 Et$_2$O/hexanes to yield after drying in vacuo at 80° C. 2.25 g solid, m.p. 176°–178° C.

ANALYSIS: Calculated for C$_{20}$H$_{24}$N$_4$O$_3$: 65.20%C, 6.57%H, 15.21%N. Found: 65.13%C, 6.59%H, 15.29%N.

EXAMPLE 9

N-(2-Propynyl)-4,5,5a,6-tetrahydro-3H-isoxazolo[5,4,3-kl]acridine-6-carboxamide

In 100 ml CCl$_4$ were combined 3.34 g 4,5,5a,6-tetrahydro-3H-isoxazolo[5,4,3-kl]acridin-6-carbamyl chloride and 1.84 ml propargylamine. The solution was refluxed 2 hours, during which a white precipitate formed. The reaction mixture was poured into ice/3N HCl and the biphasic mixture was filtered. The precipitate was recrystallized twice from MeOH/water to yield 2.00 g of product, m.p. 220° C. (decomposes).

ANALYSIS: Calculated for $C_{17}H_{15}N_3O_2$: 69.61%C, 5.15%H, 14.33%N. Found: 69.56%C, 5.29%H, 14.49%N.

EXAMPLE 10

N-[4-(1-Pyrrolidinyl)-2-butyn-1-yl]4,5,5a,6-tetrahydro-3H-isoxazolo[5,4,3-kl]acridine-6-carboxamide In 200 ml THF were combined 2.40 g N-(2-propynyl)-4,5,5a,6-tetrahydro-3H-isoxazolo[5,4,3-kl]acridin-6-carboxamide, 0.98 g paraformaldehyde, 0.75 ml pyrrolidene and a few mg of CuCl catalyst. The reaction mixture was refluxed for 1 hour, but no further reaction occurred, so again 0.98 g paraformaldehyde, 0.75 ml amine and CuCl catalyst were added. After 4 hours, the reaction was complete. The mixture was concentrated to a residue and partitioned between EtOAc and 10% NaCO₃. The EtOAc phase was dried over MgSO₄, filtered, concentrated to 100 ml and flushed through an alumina column with EtOAc. The product was concentrated to a solid, which was recrystallized twice from 1:1 DCM/hexanes and dried overnight at 80° C. to yield 2.18 g crystals, m.p. 132° C.

ANALYSIS: Calculated for $C_{22}H_{24}N_4O_2$: 70.19%C, 6.43%H, 14.88%N. Found: 69.85%C, 6.48%H, 14.86%N.

EXAMPLE 11

N-[4-(4-Morpholinyl)-2-butyn-1-yl]-4,5,5a,6-tetrahydro-3H-isoxazolo[5,4,3-kl]acridine-6-carboxamide In 200 ml THF were combined 2.35 g N-(2-propynyl)-4,5,5a,6-tetrahydro-3H-isoxazolo[5,4,3-kl]acridin-6-carboxamide, 0.96 g paraformamide, 0.77 ml morpholine and 50 mg CuCl catalyst. The reaction mixture was refluxed four hours and then paraformamide (0.96 g), morpholine (0.77 ml) and CuCl were again added. After 10 hours of reflux, the reaction mixture was concentrated and the residue partitioned between EtOAc and 10% Na₂CO₃. The EtOAc phase was dried over MgSO₄ and passed through an alumina column (about 200 g) with EtOAc eluent. As some starting material eluted with the product, the product was extracted into 3N HCl from EtOAc. The 3N HCl solution was separated, made basic and extracted into DCM. The DCM evaporated and hexanes were added to effect crystallization to yield 1.15 g powder, m.p. 186° C.

ANALYSIS: Calculated for $C_{22}H_{24}N_4O_3$: 67.33%C, 6.16%H, 14.28%N. Found: 66.99%C, 6.11%H, 14.23%N.

We claim:

1. A method of preparing a compound of the formula,

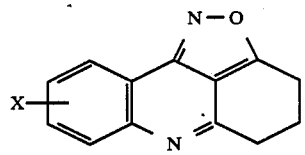

where
X is hydrogen, loweralkyl, loweralkoxy, halogen or trifluoromethyl, which comprises reacting a compound of formula

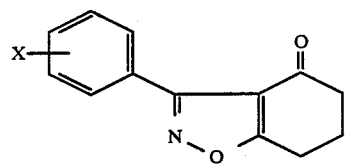

with hydrazoic acid in the presence of a protic acid or Lewis acid to afford said compound.

2. The method as defined in claim 1, which comprises allowing the compound of the formula,

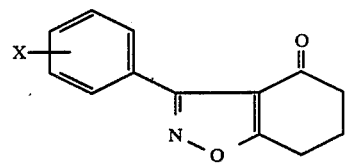

hydrazoic acid and sulfuric acid to react with each other.

* * * * *